United States Patent
Carrico-Moniz

(10) Patent No.: US 9,388,155 B1
(45) Date of Patent: *Jul. 12, 2016

(54) COUMARIN DERIVATIVES FOR CANCER THERAPY

(71) Applicant: Wellesley College, Wellesley, MA (US)

(72) Inventor: Dora Carrico-Moniz, Cambridge, MA (US)

(73) Assignee: Wellesley College, Wellesley, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/213,181

(22) Filed: Mar. 14, 2014

Related U.S. Application Data

(60) Provisional application No. 61/792,618, filed on Mar. 15, 2013.

(51) Int. Cl.
*A61K 31/35* (2006.01)
*C07D 311/18* (2006.01)

(52) U.S. Cl.
CPC .................................. *C07D 311/18* (2013.01)

(58) Field of Classification Search
None
See application file for complete search history.

(56) References Cited

U.S. PATENT DOCUMENTS

| | | | |
|---|---|---|---|
| 3,928,388 A * | 12/1975 | Reichenbacher | B01J 23/56 549/277 |
| 6,362,341 B1 | 3/2002 | Thorsett et al. | |
| 6,756,432 B2 | 6/2004 | Miyake et al. | |
| 8,168,796 B2 | 5/2012 | Mizuno et al. | |
| 8,193,241 B2 | 6/2012 | Smith, III et al. | |
| 2010/0267653 A1 | 10/2010 | Stewart | |

FOREIGN PATENT DOCUMENTS

| | | | |
|---|---|---|---|
| KR | 2010023690 | | 3/2010 |
| KR | 20100023690 A | * | 3/2010 |
| WO | WO-2007/141513 A1 | | 12/2007 |
| WO | WO-2009/006184 A1 | | 1/2009 |

OTHER PUBLICATIONS

Iranshahi et al. European Journal of Medicinal Chemistry 2012 (57) 134-142.*
Chaudhury, et al., "Studies on the Claisen Rearrangement of YY-Dimethylallyhydroxycoumarins" Journal of the Indian Chemical Society(39):783-9 (1962).
Chen, et al., "Geiparvarin Analogues: Synthesis and Anticancer Evaluation of a-Methylidene-y-butyrolactone-Bearing Coumarins", Helvetica Chimica Acta—(82): 191-197 (1999).
De Araújo, et al., "Synthesis, Structure-Activity Relationships (SAR) and in Silico Studies of Coumarin Derivatives with Antifungal Activity", Int. J. Mol. Sci. (14): 1293-1309 (2013).
Devji, et al., "Pancreatic anticancer activity of a novel geranylgeranylated coumarin derivative", Bioorganic & Medicinal Chemistry Letters (2011).
Jun, et al, "Synthesis and biological evaluation of isoprenylated coumarins as potential anti-pancreatic cancer agents", Bioorganic & Medicinal Chem. Letters (24):4645-4658 (2014).
Yukawa, et al., "The relative migratory aptitude of cyclohexyl and phenyl groups in the pinacol and the aminohydrin rearrangement", Nippon Kagaku Zasshi (1961).
Zhang, et al., "Identification of the Factors Responsible for the Selective in vitro Cytotoxic Activity of Isoprenylated Coumarin Derivatives under Nutrient-deprived Conditions", Journal of Cancer 7(2): 160-166 (2016.

* cited by examiner

*Primary Examiner* — Jeffrey S Lundgren
*Assistant Examiner* — Michael Schmitt
(74) *Attorney, Agent, or Firm* — Ropes & Gray LLP

(57) ABSTRACT

The disclosure provides methods and compositions for treating and preventing cancer using 6-substituted coumarin derivatives. The coumarin derivatives of the disclosure have substituents at the 6-position with five carbon atoms or greater. The coumarin derivatives may be further substituted and may be 3,4-dihydrocoumarins. In preferred embodiments, the coumarin derivatives of the disclosure are used to treat pancreatic cancer.

12 Claims, 2 Drawing Sheets

C-5 (Compound # 2):

C-10 (Compound # 3):

C-15 (Compound # 4):

COUMARIN DERIVATIVES FOR CANCER THERAPY

RELATED APPLICATIONS

This application claims the benefit of priority from U.S. provisional application Ser. No. 61/792,618, filed Mar. 15, 2013. The disclosure of the foregoing application is hereby incorporated by reference in its entirety.

BACKGROUND

Pancreatic cancer is one of the most devastating human cancers and is the fourth leading cause of overall cancer-related mortality in the United States. Currently, there is no clinically effective therapy for pancreatic cancer. The only chance for complete recovery is surgical resection; however, only 15-20% of patients have a resectable tumor, and of those only 20% survive up to five years after surgery. Pancreatic cancer metastasizes early and extensively, and invades surrounding tissues aggressively. In addition to its rapid progression, nearly all conventional chemotherapies and radiation treatments are ineffective against pancreatic cancer. Even when diagnosed early, patients with pancreatic cancer have <1% chance of a complete recovery. The high resistance of pancreatic cancer to available conventional chemotherapies along with its aggressive nature highlights the urgent need to develop novel effective adjunct therapies to combat this devastating cancer.

Pancreatic cancer cells are known to be remarkably tolerant to nutrient and oxygen deprivation under hypovascular conditions. Hypoxic and nutrient-deprived pancreatic cells which have adapted to survive under these conditions in tumors, both elude conventional anticancer therapies and also drive forward disease progression. Therefore, agents that eliminate the ability of cancer cells to survive under nutrient starvation conditions are potentially useful anticancer agents. In 2006, a coumarin-based natural product, angelmarin, was isolated from the root of the Japanese medicinal plant, *Angelica pubescens*. Angelmarin was found to exhibit cytotoxicity of 0.01 μg/mL against the pancreatic cancer cell line PANC-1 under nutrient starvation conditions within 24 hours.

Angelmarin is a coumarin-based natural product with a molecular formula of $C_{23}H_{20}O_6$ and a chemical name of 11-O-(p-hydroxy-cinnamoyl) columbianetin. Coumarins are ubiquitous structures present in a large number of natural compounds comprising a broad range of powerful physiological activities including anticancer, anti-viral, antifungal, anti-inflammatory, antioxidant, anticoagulant, antibacterial, antitubercular, and analgesic activities. Because of their diverse pharmacological properties, coumarins have attracted intense interest in recent years. Among these properties, the cytotoxic activities of coumarins have been the most extensively studied and coumarin compounds have served as valuable leads for further design and synthesis of more active anticancer analogues.

SUMMARY

The disclosure provides methods for treating or preventing cancer by administering a 6-substituted coumarin derivative. The substituent at the 6-position may have five or more carbon atoms such as ten or more carbon atoms, or preferably fifteen or more carbon atoms. The substituent at the 6-position may have one or more heteroatoms, such as a heteroatom selected from O, N. S, P, F, Cl, Br, and B. The coumarin derivative may also be selected from a 3,4-dihydrocoumarin.

The 6-substituted coumarin derivative may be further substituted with one or more additional substituents on the coumarin core. The one or more substituents may be independently selected at each occurrence from a substituent with five or fewer carbon atoms, or a substituent with three carbon atoms or fewer. The one or more substituents may be independently selected from alkyl, alkenyl, alkynyl, halogen, nitro, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl wherein the total number of carbon atoms in a substituent is five or fewer or three or fewer.

The substituent at the 6-position may be selected from saturated, unsaturated or partially saturated. The substituent at the 6-position may include one or more multiple bonds such as two, three four or five double bonds. The substituent at the 6-position may be branched or substituted with one or more substituents.

The substituent at the 6-position may be bound to the coumarin though a functional group linker. The functional group linker may be selected from an ether, an ester, an amide, a thioester, a thioether, a ketone, a carboxyl, a carbonate, a carbamate, a urea, a sulfonate, a sulfone, a sulfoxide, and a sulfonamide linker. The substituent at the 6-position may be bound to the coumarin through an ether, amine or thioether linkage. The substituent at the 6-position may be bound to the coumarin through an optionally substituted methylene group. The substituent at the 6-position of the coumarin may be selected from an optionally substituted isoprenyl or terpenyl ether, amine or thioether.

The coumarin derivatives of the invention may be used to inhibit proliferation or survival of a hyperproliferative cell by contacting the cell with the coumarin derivative. The coumarin derivatives may be used to inhibit survival of a cancer cell under nutrient-starved conditions by contacting the cell with the coumarin derivative. In preferred embodiments, the cancer or hyperproliferative cell is a pancreatic cancer cell.

The coumarin derivatives of the disclosure may be used to treat or prevent cancers selected from, for example, renal cell cancer, Kaposi's sarcoma, chronic leukemia, chronic lymphocytic leukemia, breast cancer, sarcoma, myeloma, ovarian carcinoma, rectal cancer, throat cancer, melanoma, lymphoma, mesothelioma, colon cancer, bladder cancer, mastocytoma, lung cancer, liver cancer, mammary adenocarcinoma, pharyngeal squamous cell carcinoma, prostate cancer, pancreatic cancer, gastrointestinal cancer, and stomach cancer. In preferred embodiments, the coumarin derivatives are used to treat or prevent pancreatic cancer.

The disclosure further provides compositions of 6-substituted coumarins or salts thereof.

DETAILED DESCRIPTION

I. Definitions

Figure 1:
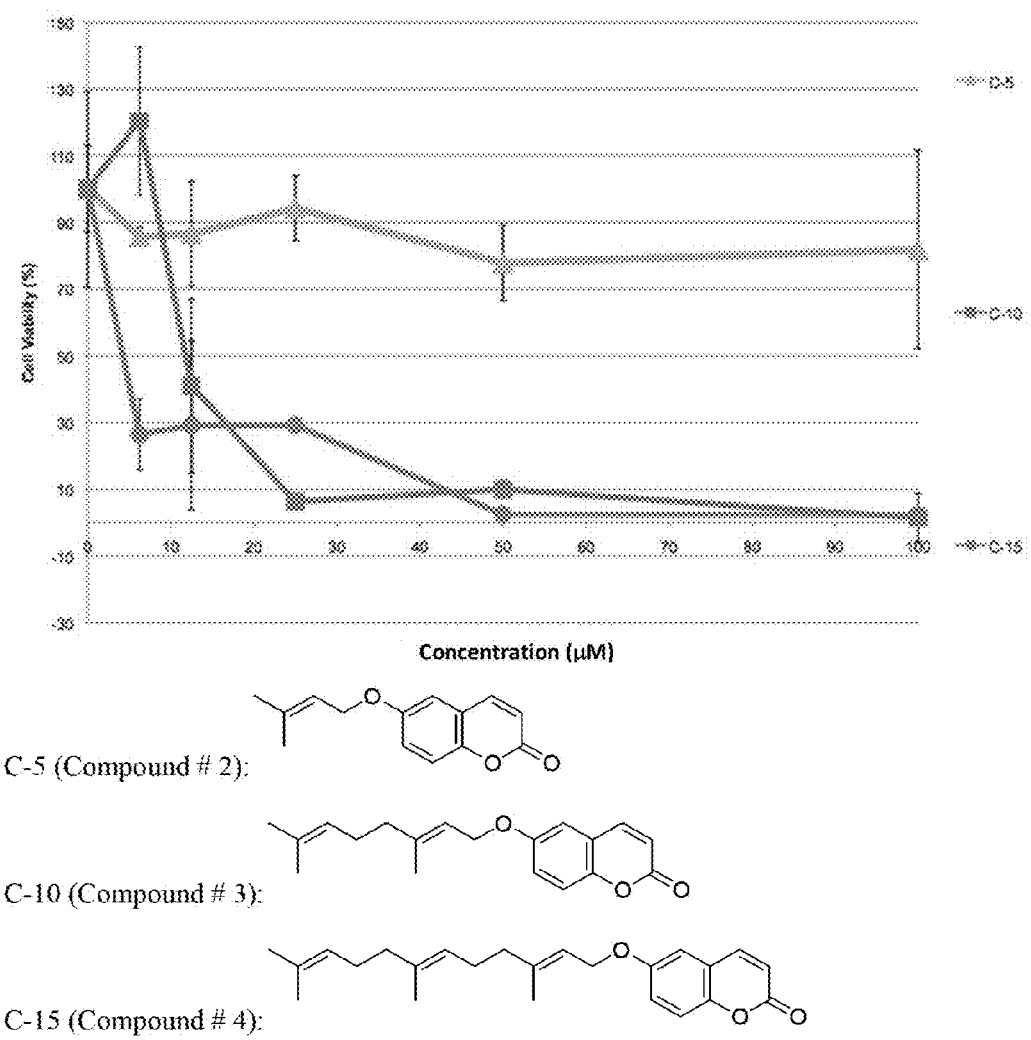
FIG. 1 depicts cell viability at different concentrations of 6-substituted coumarin derivatives measured within a 24-hour treatment period using a WST-8 cell assay.

The term "acyl" is art-recognized and refers to a group represented by the general formula hydrocarbyl-C(O)—, such as alkyl-C(O)—.

The term "acylamino" is art-recognized and refers to an amino group substituted with an acyl group and may be represented, for example, by the formula hydrocarbyl-C(O)NH—.

The term "acyloxy" is art-recognized and refers to a group represented by the general formula hydrocarbyl-C(O)O—, preferably alkyl-C(O)O—.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl, unless otherwise indicated, has 30 or fewer carbon atoms in its backbone, e.g., $C_1$-$C_{30}$ for straight chains, $C_3$-$C_{30}$ for branched chains, and more preferably 20 or fewer, e.g., $C_1$-$C_3$, $C_1$-$C_6$, $C_1$-$C_9$, $C_1$-$C_{12}$, $C_1$-$C_{15}$ and $C_1$-$C_{18}$. Likewise, preferred cycloalkyls have from 3-10 carbon atoms in their ring structure, and more preferably have 5, 6 or 7 carbons in the ring structure.

Moreover, the term "alkyl" as used throughout the specification, examples, and claims is intended to include both "unsubstituted alkyls" and "substituted alkyls", the latter of which refers to alkyl moieties having substituents replacing one or more hydrogen atoms on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" or "$C_x$ to $C_y$-alkyl" when used in conjunction with a chemical moiety, such as, acyl, acyloxy, alkyl, alkenyl, alkynyl, or alkoxy is meant to include groups that contain from x to y carbons. For example, the term "$C_x$ to $C_y$-alkyl" refers to substituted or unsubstituted saturated hydrocarbon groups, including straight-chain alkyl and branched-chain alkyl groups that contain from x to y carbons, including haloalkyl groups such as trifluoromethyl and 2,2,2-trifluoroethyl, etc. The terms "$C_x$ to $C_y$-alkenyl" and "$C_x$ to $C_y$-alkynyl" refer to substituted or unsubstituted unsaturated aliphatic groups analogous in length and possible substitution to the alkyls described above, but that contain at least one double or triple bond respectively. Within a range of $C_{x-y}$, subranges are also generally envisioned. For example, for the range $C_1$ to $C_{15}$-alkyl, ranges falling within this range such as $C_1$ to $C_2$-alkyl and $C_2$ to $C_8$-alkyl are also included.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

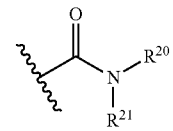

wherein $R^{20}$ and $R^{21}$ each independently represent a hydrogen or hydrocarbyl group, or $R^{20}$ and $R^{21}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

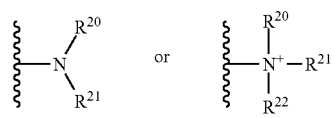

wherein $R^{20}$, $R^{21}$, and $R^{22}$ each independently represent a hydrogen or a hydrocarbyl group, or $R^{20}$ and $R^{21}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which one or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

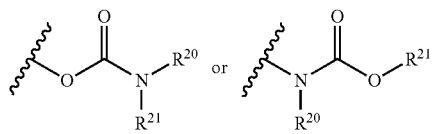

wherein $R^{20}$ and $R^{21}$ independently represent hydrogen or a hydrocarbyl group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —OCO₂—$R^{20}$, wherein $R^{20}$ represents a hydrocarbyl group.

The term "carboxyl", as used herein, refers to a group represented by the formula —CO₂H.

The term "ester", as used herein, refers to a group —C(O)OR²⁰ wherein $R^{20}$ represents a hydrocarbyl group such as an aryl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The term "haloalkyl" as used herein includes from one halo substituent up to perhalo substitution. Exemplary haloalkyls includes —CFH₂, —CClH₂, —CBrH₂, —CF₂H, —CCl₂H, —CBr₂H, —CF₃, —CCl₃, —CBr₃, —CH₂CH₂F, —CH₂CH₂Cl, —CH₂CH₂Br, —CH₂CHF₂, —CHFCH₃, —CHCl CH₃, —CHBrCH₃, —CF₂CHF₂, —CF₂CHCl₂, —CF₂CHBr₂, —CH(CF₃)₂, and —C(CF₃)₃. Perhaloalkyl includes, for example, —CF₃, —CCl₃, —CBr₃, —CF₂CF₃, —CCl₂CF₃ and —CBr₂CF₃.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, such as 5-membered rings whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Exemplary heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 8-membered rings, whose ring structures include at least one heteroatom, preferably one to four heteroatoms, more preferably one or two heteroatoms. The terms "heterocyclyl", "heterocycle" and "heterocyclic" also include polycyclic ring systems having two or more cyclic rings in which one or more carbons are common to two adjoining rings wherein at least one of the rings is heterocyclic, e.g., the other cyclic rings can be selected from cycloalkyl, cycloalkenyl, cycloalkynyl, aryl, heteroaryl, and/or heterocyclyl. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to optionally substituted alkyl, alkenyl, alkynyl, carbocycle and aryl and combinations thereof.

The term "hydroxyl" or "hydroxy", as used herein, refers to an OH group.

The term "hydroxyalkyl", as used herein, refers to an alkyl group substituted with a hydroxy group.

The term "including" is used to mean "including but not limited to".

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "prodrug" is intended to encompass compounds which, under physiologic conditions, are converted into the therapeutically active agents of the present disclosure (e.g., a compound of Formula I, II, or III). A common method for making a prodrug is to include one or more selected moieties which are hydrolyzed under physiologic conditions to reveal the desired molecule. In other embodiments, the prodrug is converted by an enzymatic activity of the host animal. For example, esters (e.g., esters of alcohols or carboxylic acids) are possible prodrugs of the present disclosure. In certain embodiments disclosed herein (e.g., the various compositions and methods), some or all of the compounds of Formula I, II, or III can be replaced with a suitable prodrug, e.g., wherein a hydroxyl or carboxylic acid present in the parent compound is presented as an ester.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted at a position can themselves be substituted, if appropriate.

The term "sulfate" is art-recognized and refers to the group —OSO$_3$H, or a pharmaceutically acceptable salt thereof.

The term "sulfonamide" is art-recognized and refers to the group represented by the general formula

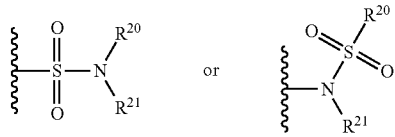

wherein R$^{20}$ and R$^{21}$ independently represents hydrogen or hydrocarbyl.

The term "sulfoxide" is art-recognized and refers to the group —S(O)—R$^{20}$, wherein R$^{20}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{20}$, wherein R$^{20}$ represents a hydrocarbyl.

The term "thioalkyl", as used herein, refers to an alkyl group substituted with a thiol group.

The term "thioester", as used herein, refers to a group —C(O)SR$^{20}$ or —SC(O)R$^{20}$ wherein R$^{20}$ represents a hydrocarbyl.

The term "thioether", as used herein, is equivalent to an ether, wherein the oxygen is replaced with a sulfur.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "urea" is art-recognized and may be represented by the general formula

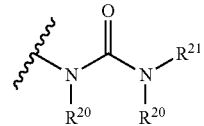

wherein R$^{20}$ and R$^{21}$ independently represent hydrogen or a hydrocarbyl.

II. Coumarin Derivatives of the Disclosure

The disclosure provides 6-substituted coumarin derivatives. As referred to herein the "6-substituent" of the coumarin derivative and the "substituent at the 6-position" of the coumarin derivative are used interchangeably and refer to a group bound to the 6-position of the coumarin core structure. The 6-substituted coumarin derivatives may include a substituent at the 6-position with at least five carbon atoms, such as ten or more carbon atoms or even fifteen or more carbon atoms. In certain embodiments, the 6-substituted coumarins of the disclosure may include a substituent at the 6-position with twenty or more carbons. The coumarin derivatives of the disclosure may be selected from an optionally substituted 6-substituted coumarin represented by Formula (I):

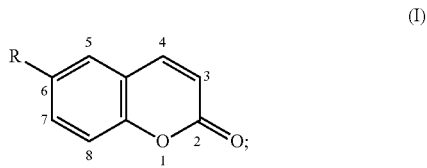

or a salt thereof, wherein R represents the 6-substituent described herein.

The coumarin derivative of the disclosure may be selected from an optionally substituted 6-substituted 3,4-dihydrocoumarin represented by the Formula (II):

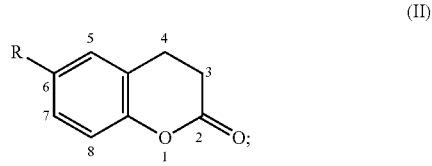

or a salt thereof, wherein R represents the 6-substituent described herein.

The 6-substituent may include one or more heteroatoms such as heteroatoms selected from O, N, S, P, F, Cl, Br, and B. Preferably, the 6-substituent may include one or more of O, N, S, F, Cl and Br. As an example, the substituent in the 6-position of the coumarin derivative may have fifteen or more carbons and one or more heteroatoms selected from N, O, S, and F.

The 6-substituent may include an optionally substituted carbon chain with two or more carbons bound without intervening heteroatoms. The 6-substituent may include an optionally substituted carbon chain selected from saturated, unsaturated or partially saturated aliphatic chains. For example, the 6-substituent may contain a carbon chain without carbon-carbon multiple bonds. The 6-substituent may contain a carbon chain with one or more multiple carbon-carbon bonds, such as one or more double bonds. The 6-substituent may contain a carbon chain with one or more carbon-carbon multiple bonds with one or more intervening saturated carbons in a chain, such as two or more intervening saturated carbons in a chain. The carbon chain may be selected from an optionally substituted $C_{2-25}$ alkyl chain, an optionally substituted $C_{2-25}$ alkenyl chain, an optionally substituted $C_{2-25}$ alkynyl chain, or a $C_{2-25}$ carbon chain with two or more multiple bonds of the same or differing types. The optionally substituted carbon chain may include five carbon atoms or more, ten carbon atoms or more, 15 carbon atoms or more or 20 carbon atoms or more.

The 6-substituent may itself be substituted by one or more substituents. Substituents may be selected from alkenyl, alkynyl, halogen, nitro, cyano, carboxyl, sulfate, amino, alkoxy, alkylamino, alkylthio, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, and carbocyclylalkyl.

In addition to the 6-substituent, the coumarin derivative may be substituted at one or more additional positions on the coumarin core. As an example, in addition to the substitution at the 6-position of the coumarin, the coumarin derivative may be substituted at one or more of the 3-, 4-, 5-, 7- and 8-positions of the coumarin core. For example, the coumarin derivative may be substituted with a substituent at the 6-position and at the 8-position.

The substituents at any one or more of positions 3, 4, 5, 7, and 8 of the coumarin core of the coumarin derivative may be independently selected at each position from hydrogen, alkyl, alkenyl, alkynyl, halogen, nitro, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl. When the coumarin derivative is 6-substituted 3,4-dihydrocoumarin, any one or more of the hydrogens at the 3- and 4-position of the coumarin derivative may be substituted. For example, a 6-substituted 3,4-dihydrocoumarin may be substituted at the 3-position with two fluoro atoms, or a methoxy group and a methyl group. A 6-substituted 3,4-dihydrocoumarin may be substituted at the 3-position with an alkyl group and the 4-position with a methoxy group and a methyl group. A 6-substituted 3,4-dihydrocoumarin may be substituted by one or more substituents at any one or more of positions 3, 4, 5, 7, and 8 of the coumarin core.

In certain such embodiments, the substituents located at positions 3, 4, 5, 7, and 8 of the coumarin derivative independently at each occurrence are selected from groups with five carbon atoms or fewer. Substituents with five carbons or fewer may contain other heteroatoms such as O, N, S, F, Cl, and Br, one or more multiple bonds, and one or more functional groups. For example, a substituent with five carbons or fewer includes: hydrogen, halo, cyano, nitro, $C_{1-5}$ alkyl, $C_{1-5}$ alkenyl, $C_{1-5}$ alkynyl, $C_{1-5}$ alkoxy, halo $C_{1-5}$ alkyl, halo $C_{1-5}$ alkoxy, amino $C_{1-5}$ alkyl, dimethylamino $C_{1-3}$ alkyl, methoxy $C_{1-4}$ alkyl, and $C_{1-5}$ alkylamino. In preferred embodiments, the substituent with five carbon atoms or fewer is selected from hydrogen, halo, cyano, $C_{1-5}$ alkyl, $C_{1-5}$ alkenyl, $C_{1-5}$ alkynyl, $C_{1-5}$ alkoxy and halo $C_{1-5}$ alkyl.

The substituents at any of positions 3, 4, 5, 7, and 8 of the core of the coumarin derivative may be selected independently at each occurrence from groups with three carbon atoms or fewer. Substituents with three carbons or fewer may contain other heteroatoms such as O, N, S, F, Cl, and Br, one or more multiple bonds, and one or more functional groups. For example, a substituent with three carbons or fewer includes: hydrogen, halo, cyano, nitro, $C_{1-3}$ alkyl, $C_{1-3}$ alkenyl, $C_{1-3}$ alkynyl, $C_{1-3}$ alkoxy, halo $C_{1-3}$ alkyl, halo $C_{1-3}$ alkoxy, amino $C_{1-3}$ alkyl, dimethylamino methyl, methoxy $C_{1-2}$ alkyl, and $C_{1-3}$ alkylamino.

The 6-substituent may be bound to the coumarin through a functional group linker. The functional group linker may be selected from any functional group such as an ether, an ester, an amide, a thioester, a thioether, a ketone, a carboxyl, a carbonate, a carbamate, a urea, a sulfonate, a sulfone, a sulfoxide, and a sulfonamide linker. The linker preferably includes three or fewer atoms such as a one-atom linker like oxygen or sulfur, or a two-atom linker such as NH. In certain embodiments, a carbon chain of the substituent may be bound to the coumarin through an ether, amine or thioether linkage. A carbon chain of the substituent at the 6-position may be bound to the coumarin core through an optionally substituted methylene group.

The 6-substituent may include an optionally substituted isoprene or terpene. The term "terpene" or "terpenyl", as used herein, refers to acyclic oligomers of isoprene units. Exemplary terpenes include monoterpenes, sesquiterpenes, diterpenes, sesterpenes, triterpenes, sesquarterpenes, and tetraterpenes. The 6-substituent may include, for example, optionally substituted monoterpenes, sequiterpenes, or diterpenes. The 6-substituent may be selected from optionally substituted monoterpenes, sequiterpenes, or diterpenes bound to the coumarin through a functional group such as an ether, thioether or amine. The 6-substituent may be selected from optionally substituted monoterpenes, sequiterpenes, or diterpenes bound to the coumarin through an optionally substituted methylene group.

The 6-substituent may include one or more groups selected from an isoprenyl group, a terpenyl group, an ether, an amine or a thioether. The substituent at the 6-position may include both an ether and an isoprenyl or terpenyl group, such as an isoprenyl ether or a terpenyl ether. The substituent at the 6-position may include both an amine and an isoprenyl or terpenyl group, such as an isoprenyl amino group or a terpenyl amino group. The substituent at the 6-position may include both a thioether and an isoprenyl or terpenyl group, such as an isoprenyl thioether or a terpenyl thioether.

The coumarin derivative of the disclosure may be represented by Formula (III):

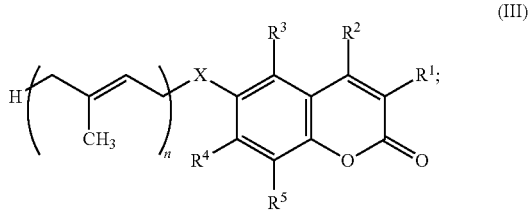

(III)

or a salt thereof, wherein as valence and stability permit:

X is selected from —NR⁶—, —O—, or —S—;

$R^1$, $R^2$, $R^3$, $R^4$, and $R^5$ are independently selected at each occurrence from hydrogen, halo, nitro, sulfate, and an optionally substituted $C_{1-5}$ group;

$R^6$ is selected from hydrogen or optionally substituted alkyl, such as a lower alkyl; and n is selected from 1 to 6.

In certain embodiments, the optionally substituted $C_{1-5}$ group is selected from cyano, amino, alkyl, alkenyl, alkynyl, alkoxy, alkylamino, alkylthio, hydroxyalkyl, alkoxyalkyl, haloalkyl, aminoalkyl, thioalkyl, ether, thioether, ester, amide, thioester, carbonate, carbamate, urea, sulfone, sulfoxide, sulfonamide, acyl, acyloxy, acylamino, heteroaryl, carbocyclyl, heterocyclyl, hetaralkyl, carbocyclylalkyl, and heterocyclylalkyl wherein the total number of carbon atoms in a group is selected from 1 to 5 carbon atoms. In certain such embodiments, the $C_{1-5}$ group may be selected from cyano, amino, alkyl, alkenyl, alkynyl, alkoxy, alkylamino, alkylthio, hydroxyalkyl, alkoxyalkyl, haloalkyl, aminoalkyl, thioalkyl, ether, thioether, ester, and amide.

$R^6$ may be selected from hydrogen, haloalkyl or alkyl. In certain such embodiments, $R^6$ is selected from hydrogen and alkyl. When $R^6$ is selected from hydrogen and alkyl, the $C_{1-5}$ group may be selected from cyano, amino, alkyl, alkenyl, alkynyl, alkoxy, alkylamino, alkylthio, hydroxyalkyl, alkoxyalkyl, haloalkyl, aminoalkyl, thioalkyl, ether, thioether, ester, and amide. In certain embodiments, X is —NR⁶—, $R^6$ is selected from hydrogen, haloalkyl or alkyl and $R^1$, $R^2$, $R^3$, $R^4$, and $R^5$ are independently selected at each occurrence from hydrogen, halo, nitro, sulfate, and a $C_{1-5}$ group selected from cyano, amino, alkyl, alkenyl, alkynyl, alkoxy, alkylamino, alkylthio, hydroxyalkyl, alkoxyalkyl, haloalkyl, aminoalkyl, thioalkyl, ether, thioether, ester, and amide. In such embodiments, n may be selected from 2 to 5, such as 3 to 5, such as 4 to 5. In certain embodiments, X may be —NR⁶—, $R^6$ may be selected from hydrogen, haloalkyl or alkyl, $R^1$, $R^2$, $R^3$, $R^4$, and $R^5$ are independently selected at each occurrence from hydrogen, halo, and a $C_{1-5}$ group selected from cyano, amino, alkyl, alkenyl, alkynyl, and alkoxy, and n may be selected from 3 to 5, such as 4 to 5.

X may be selected from —O— or —S—. When X is —O—, $R^1$, $R^2$, $R^3$, $R^4$, and $R^5$ may be independently selected at each occurrence from hydrogen, halo, nitro, sulfate, and a $C_{1-5}$ group selected from cyano, amino, alkyl, alkenyl, alkynyl, alkoxy, alkylamino, alkylthio, hydroxyalkyl, alkoxyalkyl, haloalkyl, aminoalkyl, thioalkyl, ether, thioether, ester, and amide, and n may be selected from 2 to 5, such as 3 to 5, such as 4 to 5. In certain embodiments, X may be —O—, $R^1$, $R^2$, $R^3$, $R^4$, and $R^5$ may be independently selected at each occurrence from hydrogen, halo, and a $C_{1-5}$ group selected from cyano, amino, alkyl, alkenyl, alkynyl, and alkoxy, and n may be selected from 3 to 5, such as 4 to 5.

When X is —S—, $R^1$, $R^2$, $R^3$, $R^4$, and $R^5$ may be independently selected at each occurrence from hydrogen, halo, nitro, sulfate, and a $C_1$ to $C_5$ group selected from cyano, amino, alkyl, alkenyl, alkynyl, alkoxy, alkylamino, alkylthio, hydroxyalkyl, alkoxyalkyl, haloalkyl, aminoalkyl, thioalkyl, ether, thioether, ester, and amide, and n may be selected from 2 to 5, such as 3 to 5, such as 4 to 5. In certain embodiments, X may be —S—, $R^1$, $R^2$, $R^3$, $R^4$, and $R^5$ may be independently selected at each occurrence from hydrogen, halo, and a $C_{1-5}$ group selected from cyano, amino, alkyl, alkenyl, alkynyl, and alkoxy, and n may be selected from 3 to 5, such as 4 to 5.

In preferred embodiments, the coumarin derivative of the disclosure is selected from:

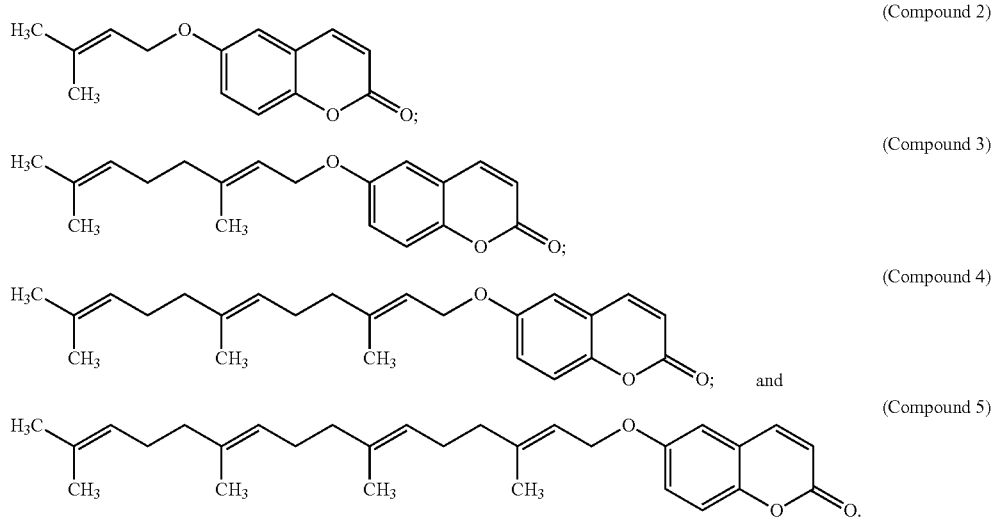

III. Methods of the Disclosure

The disclosure contemplates using any of the coumarin derivatives in any of the methods described herein. Hyperproliferative disorders such as psoriasis, rheumatoid arthritis and cancer involve unwanted cellular proliferation. Inhibiting proliferation of a hyperproliferative cell may be directed to preventing further growth of cells and actively inducing the destruction of the pathological cells. The induction of apoptosis, or programmed cell death, is a common mode of operation for several classes of anticancer drugs. The coumarin derivatives of the disclosure may be used for inhibiting proliferation or survival of a hyperproliferative cell by contacting the cell with a coumarin derivative. In preferred embodiments, the hyperproliferative cell is a cancer cell such as a pancreatic cancer cell.

The coumarin derivatives of the disclosure may be effective in treating a variety of diseases related to unwanted cell proliferation. Such hyperproliferative diseases include but are not limited to: psoriasis, rheumatoid arthritis, lamellar ichthyosis, epidermolytic hyperkeratosis, restenosis, endometriosis, proliferative retinopathy, lung fibrosis, desmoids or abnormal wound healing.

The disclosure provides methods for treating or preventing cancer in a subject in need thereof, by administering a coumarin derivative, wherein the coumarin derivative is substituted with at least one substituent at the 6-position. The coumarin derivatives of the disclosure may be effective in treatment of various types of cancers, including but not limited to: pancreatic cancer, renal cell cancer, Kaposi's sarcoma, chronic leukemia (preferably chronic myelogenous leukemia), chronic lymphocytic leukemia, breast cancer, sarcoma, ovarian carcinoma, rectal cancer, throat cancer, melanoma, colon cancer, bladder cancer, lymphoma, mesothelioma, mastocytoma, lung cancer, liver cancer, mammary adenocarcinoma, pharyngeal squamous cell carcinoma, gastrointestinal cancer, stomach cancer, myeloma, prostate cancer, B-cell malignancies or metastatic cancers. In preferred embodiments, the disclosure provides a method for treating or preventing pancreatic cancer, such as adenocarcinoma or pancreatic neuroendocrine tumors. Preventing cancer includes, for example, preventing the reoccurrence of cancer once a cancer is in remission.

A defining feature of solid tumors is their capacity to divide aggressively and disseminate metastases under conditions of nutrient deprivation and limited oxygen availability. These severe stresses arise from inadequate perfusion as the primary tumor rapidly outgrows its initial blood supply, and from dramatic structural abnormalities of tumor vessels that can lead to disturbed microcirculation (Hockel and Vaupel, *Semin. Oncol.* 28(2 Suppl 8):36-41, 2001; Vaupel, et al. *Med. Oncol.* 18:243-59, 2001). As a result, regions of low $O_2$ tension, or hypoxia, are heterogeneously distributed within the tumor mass. While tumor hypoxia is a physiological barrier to cell survival, it paradoxically drives malignant progression by imposing a powerful selective pressure for cells that can best adapt to this stress and subsequently resume cell division. In certain embodiments, the coumarin derivatives of the disclosure are used to inhibit survival of a cancer cell under nutrient starvation conditions, comprising contacting the cell with a coumarin derivative. Nutrient-deprived conditions may include nutrient and/or oxygen deprivation. The coumarin derivatives of the disclosure may be used to inhibit survival of hypoxic tumor cells. In preferred embodiments, the coumarin derivatives of the disclosure are used to inhibit survival of pancreatic cancer cells under nutrient starvation conditions.

The methods of the disclosure may be in vitro methods where the cell is a cell in culture. In other embodiments, the method is an in vivo method and contacting the cell comprises administering the coumarin derivative to a subject in need thereof.

In certain embodiments, the coumarin derivatives are cytotoxic to cancer cells. In such embodiments, coumarin derivatives have an $LD_{50}$ to cancer cells of about 100 µM or less, about 75 µM or less, about 50 µM or less, about 25 µM or less, about 15 µM or less or even about 10 µM or less. In preferred embodiments the $LD_{50}$ is between 2 and 25 µM, such as between 2 and 15 µM, or even between 2 and 13 µM. In certain such embodiments, the cytotoxicity occurs under nutrient-deprived conditions. The term "$LD_{50}$" is art-recognized. In certain embodiments, $LD_{50}$ means the dose of a drug which is lethal in 50% of test subjects.

The coumarin derivatives of the disclosure may have a greater cytotoxicity to cancer cells as compared to angelmarin. For example, the coumarin derivatives of the disclosure may exhibit about 10% or more greater cytotoxicity, such as about 20% or more greater cytotoxicity, or even 50% or more greater cytotoxicity of cancer cells relative to angelmarin. In preferred embodiments, the coumarin derivatives of the disclosure exhibit a cytotoxicity of 25 µM or less, 20 µM or less, 15 µM or less or even 10 µM or less. In particular embodiments, the coumarin derivatives of the disclosure exhibit a cytotoxicity of 6 µM or less, such as about 5 µM. In certain embodiments, the coumarin derivatives of the disclosure exhibit a cytotoxicity of 5 µg/mL or less, such as 4 µg/mL or less, or even 2 µg/mL or less. The coumarin derivatives of the disclosure may exhibit a cytotoxicity of about 2 µg/mL or less against a nutrient-deprived cancer cell line.

In one embodiment, the method of treating or preventing cancer, such as pancreatic cancer, may comprise administering a compound of the disclosure conjointly with one or more other chemotherapeutic agent(s). Chemotherapeutic agents that may be conjointly administered with compounds of the disclosure include: aminoglutethimide, amsacrine, anastrozole, asparaginase, bcg, bicalutamide, bleomycin, bortezomib, buserelin, busulfan, campothecin, capecitabine, carboplatin, carfilzomib, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, plicamycin, porfimer, procarbazine, raltitrexed, rituximab, sorafenib, streptozocin, sunitinib, suramin, tamoxifen, temozolomide, temsirolimus, teniposide, testosterone, thioguanine, thiotepa, titanocene dichloride, topotecan, trastuzumab, tretinoin, vinblastine, vincristine, vindesine, and vinorelbine. In certain embodiments of the methods of the disclosure described herein, the chemotherapeutic agent conjointly administered with compounds of the disclosure is a taxane chemotherapeutic agent, such as paclitaxel or docetaxel. In certain embodiments of the methods of the disclosure described herein, the chemotherapeutic agent conjointly administered with compounds of the disclosure is doxorubicin. In certain embodiments of the methods of the disclosure described herein, a compound of the disclosure is administered conjointly with a taxane chemotherapeutic agent (e.g., paclitaxel) and doxorubicin. Many combination therapies have been developed for the treatment of cancer. In certain embodiments, compounds of the disclosure may be conjointly administered with a combination therapy.

In certain embodiments, a compound of the disclosure may be conjointly administered with non-chemical methods of cancer treatment. In certain embodiments, a compound of the disclosure may be conjointly administered with radiation therapy. In certain embodiments, a compound of the disclosure may be conjointly administered with surgery, with thermoablation, with focused ultrasound therapy, with cryotherapy, or with any combination of these.

In certain embodiments, different compounds of the disclosure may be conjointly administered with one or more other compounds of the disclosure. Moreover, such combinations may be conjointly administered with other therapeutic agents, such as other agents suitable for the treatment of cancer, immunological or neurological diseases, such as the agents identified above.

In certain embodiments, the present disclosure provides a kit comprising: a) one or more single dosage forms of a compound of the disclosure; b) one or more single dosage forms of a chemotherapeutic agent as mentioned above; and c) instructions for the administration of the compound of the disclosure and the chemotherapeutic agent for the treatment of cancer, wherein the cancer is selected from pancreatic cancer, breast cancer, colorectal cancer, endocrine cancer, melanoma, renal cancer and B cell malignancy.

The present disclosure provides a kit comprising:
a) a pharmaceutical formulation (e.g., one or more single dosage forms) comprising a compound of the disclosure; and
b) instructions for the administration of the pharmaceutical formulation, e.g., for treating or preventing cancer, such as pancreatic cancer (such as pancreatic adenocarcinoma or pancreatic neuroendocrine tumors), breast cancer, colorectal cancer, endocrine cancer, melanoma, renal cancer or B cell malignancy.

The present disclosure provides a kit comprising:
a) a pharmaceutical formulation (e.g., one or more single dosage forms) comprising a compound of the disclosure; and
b) instructions for the administration of the pharmaceutical formulation, e.g., for treating or preventing pancreatic cancer (such as pancreatic adenocarcinoma or pancreatic neuroendocrine tumors), breast cancer, wherein the breast cancer comprises basal-type breast cancer cells, triple-negative breast cancer cells, or claudin-low breast cancer cells.

In certain embodiments, the kit further comprises instructions for the administration of the pharmaceutical formulation comprising a compound of the disclosure conjointly with a chemotherapeutic agent as mentioned above. In certain embodiments, the kit further comprises a second pharmaceutical formulation (e.g., as one or more single dosage forms) comprising a chemotherapeutic agent as mentioned above.

IV. Pharmaceutical Compositions of the Disclosure

The disclosure contemplates using any of the coumarin derivatives of Formulas (I), (II), or (III) or salts thereof in any of the compositions described herein. The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a 6-substituted coumarin derivative of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a coumarin derivative of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a selfmicroemulsifying drug delivery system. The pharmaceutical composition also can be a liposome or other polymer matrix, which can have incorporated therein, for example, a coumarin derivative of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The coumarin derivative may also be formulated for inhalation. In certain embodiments, a coumarin derivative may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the coumarin derivative which produces a therapeutic effect. Generally, out of one hundred percent, this amount will range from about 1 percent to about ninety-nine percent of active ingredient, such as from about 5 percent to about 70 percent.

Methods of preparing these formulations or compositions include the step of bringing into association an active compound, such as a coumarin derivative of the disclosure, with the carrier and, optionally, one or more accessory ingredients. In general, the formulations may be prepared by uniformly and intimately bringing into association a coumarin derivative of the present disclosure with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a coumarin derivative of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a coumarin derivative of the present disclosure to the body. Such dosage forms can be made by dissolving or dispersing the active coumarin derivative in the proper medium. Absorption enhancers can also be used to increase the flux of the compound across the skin. The rate of such flux can be controlled by either providing a rate controlling membrane or dispersing the coumarin derivative in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject coumarin derivatives in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a coumarin derivative at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered one or more times daily.

The patient receiving this treatment is any animal in need, including primates, in particular humans, and other mammals such as equines, cattle, swine and sheep; and poultry and pets in general.

In certain embodiments, coumarin derivatives of the disclosure may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of coumarin derivatives of the disclosure with one or more additional therapeutic agent(s) (e.g., one or more additional chemotherapeutic agent(s)) provides improved efficacy relative to each individual administration of the compound of the disclosure (e.g., compound of formula I, II or III) or the one or more additional therapeutic agent(s). In certain such embodiments, the conjoint administration provides an additive effect, wherein an additive effect refers to the sum of each of the effects of individual administration of the compound of the disclosure and the one or more additional therapeutic agent(s).

This disclosure includes the use of pharmaceutically acceptable salts of coumarin derivatives of the disclosure in the compositions and methods of the present disclosure. In certain embodiments, contemplated salts of the disclosure include, but are not limited to, alkyl, dialkyl, trialkyl or tetraalkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In certain embodiments, the disclosure relates to a method for conducting a pharmaceutical business, by manufacturing a formulation of a coumarin derivative of the disclosure, or a kit as described herein, and marketing to healthcare providers the benefits of using the formulation or kit for treating or preventing any of the diseases or conditions as described herein.

In certain embodiments, the disclosure relates to a method for conducting a pharmaceutical business, by providing a distribution network for selling a formulation of a coumarin derivative of the disclosure, or kit as described herein, and providing instruction material to patients or physicians for using the formulation for treating or preventing any of the diseases or conditions as described herein.

In certain embodiments, the disclosure comprises a method for conducting a pharmaceutical business, by determining an appropriate formulation and dosage of a coumarin derivative of the disclosure for treating or preventing any of the diseases or conditions as described herein, conducting therapeutic profiling of identified formulations for efficacy and toxicity in animals, and providing a distribution network for selling an identified preparation as having an acceptable therapeutic profile. In certain embodiments, the method further includes providing a sales group for marketing the preparation to healthcare providers.

In certain embodiments, the disclosure relates to a method for conducting a pharmaceutical business by determining an appropriate formulation and dosage of a coumarin derivative of the disclosure for treating or preventing any of the disease or conditions as described herein, and licensing, to a third party, the rights for further development and sale of the formulation.

EQUIVALENTS

The present disclosure provides among other things methods and compositions for treating or preventing cancer. While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications and patents mentioned herein, including any items listed below, are hereby incorporated by reference in their entirety as if each individual publication or patent was specifically and individually indicated to be incorporated by reference. In case of conflict, the present application, including any definitions herein, will control.

EXAMPLES

Figure 2:
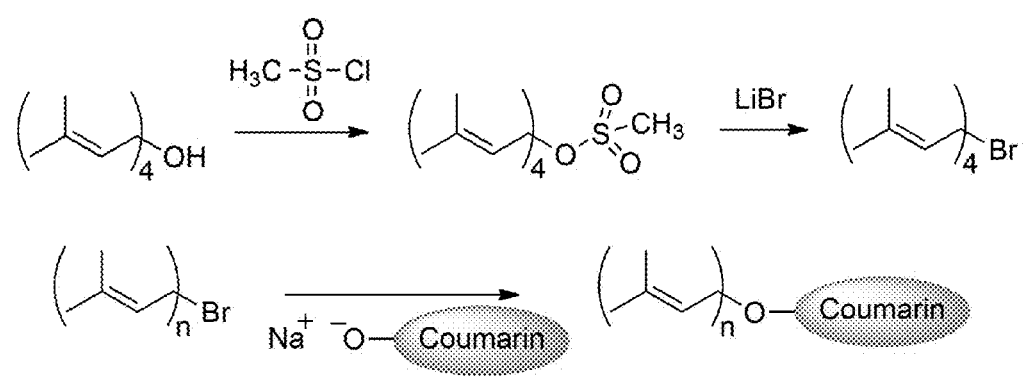
FIG. 2 depicts an exemplary synthetic approach to preparing the substituted coumarins of the disclosure.

An exemplary scheme for preparing compounds of the disclosure may be found in FIG. 2.

TABLE 1

6-Substituted Coumarin Derivatives

| Compound # | R |
|---|---|
| 1 | OH |
| 2 | —O—CH$_2$—CH=C(CH$_3$)$_2$ (prenyl) |
| 3 | —O—geranyl |
| 4 | —O—farnesyl |
| 5 | —O—geranylgeranyl |

Example 1

Synthesis of 6-((3-methylbut-2-en-1-yl)oxy)-2H-chromen-2-one (2)

An oven-dried 50 mL round bottom flask was prepared with a magnetic stirring bar, a rubber septum cover, and a nitrogen inlet. 6-hydroxycoumarin (1) (114 mg, 0.7 mmol) and 4 mL of anhydrous N,N-dimethylformamide (DMF) were added to the round bottom flask. The solution was stirred and cooled to 0° C. in a salt-ice bath. Sodium hydride (28 mg of 60% mineral oil suspension, 0.7 mmol) was added to the flask and the solution was kept stirring at 0° C. for 30 minutes. 3,3-dimethylallyl bromide (192 µL, 1.66 mmol) in 1 mL of anhydrous DMF was cooled to 0° C. and added drop-wise to the flask through the rubber septum using a syringe. The reaction mixture was left stirring under nitrogen at room temperature for 14 hours. The desired product was isolated via column chromatography using a solvent system of 100% Hexanes, 20:1 Hexanes:Ethyl acetate, 15:1 Hexanes:Ethyl acetate, 10:1 Hexanes:Ethyl acetate, 7:3 Hexanes:Ethyl acetate, and 2:1 Hexanes:Ethyl acetate. The purified product was characterized by NMR spectroscopy ($^1$H-NMR, $^{13}$C-NMR) and high-resolution mass spectrometry (HRMS). $^1$H-NMR (300 MHz, CDCl$_3$): ∂ 1.76-1.87 (6H), 4.54 (d, 2H, J=6 Hz), 5.50 (m, 1H), 6.43 (m, 1H), 6.92-7.67 (4H); $^{13}$C-NMR (75 MHz, CDCl$_3$): ∂ 18.68, 26.27, 65.86, 111.35, 117.42, 118.26, 119.44, 119.54, 120.53, 139.38, 143.69, 148.80, 155.71, 161.47. HRMS (ES) Calcd. for C$_{14}$H$_{15}$O$_3$: 231.1021. found: 231.1024.

Example 2

Synthesis of (E)-6-((3,7-dimethylocta-2,6-dien-1-yl)oxy)-2H-chromen-2-one (3)

An oven-dried 50 mL round bottom flask was prepared with a magnetic stirring bar, a rubber septum cover, and a nitrogen inlet. 6-hydroxycoumarin (1) (114 mg, 0.7 mmol) and 4 mL of anhydrous DMF were added to the round bottom flask. The solution was stirred and cooled to 0° C. in a salt-ice bath. Sodium hydride (28 mg of 60% mineral oil suspension, 0.7 mmol) was added to the flask and the solution was kept stirring at 0° C. for 30 minutes. Geranyl bromide (329 µL, 1.66 mmol) in 1 mL of anhydrous DMF was cooled to 0° C. and added dropwise to the flask through the rubber septum using a syringe. The reaction mixture was left stirring under nitrogen at room temperature for 14 hours. The desired product was isolated by column chromatography using a solvent system of 100% Hexanes, 20:1 Hexanes:Ethyl acetate, 15:1 Hexanes:Ethyl acetate, 10:1 Hexanes:Ethyl acetate, 7:3 Hexanes:Ethyl acetate, and 2:1 Hexanes:Ethyl acetate. The purified product was characterized by NMR spectroscopy ($^1$H-NMR, $^{13}$C-NMR) and high-resolution mass spectrometry (HRMS). $^1$H-NMR (300 MHz, CDCl$_3$): ∂ 1.61-1.84 (9H), 2.13 (m, 4H), 4.57 (d, 2H, J=6 Hz), 5.1 (m, 1H), 5.48 (t, 1H), 6.43 (d, 1H, J=9 Hz), 6.93-7.67 (4H); $^{13}$C-NMR (75 MHz, CDCl$_3$): ∂ 18.0, 18.2, 26.25, 26.38, 39.06, 65.20, 111.08, 117.01, 117.83, 118.89, 119.14, 119.70, 123.88, 131.94, 141.44, 143.27, 148.41, 155.33, 161.06. HRMS (CI) Calcd. for C$_{19}$H$_{23}$O$_3$: 299.16473. found: 299.16377.

Example 3

Synthesis of 6-(((2E,6E)-3,7,11-trimethyldodeca-2,6,10-trien-1-yl)oxy)-2H-chromen-2-one (4)

An oven-dried 50 mL round bottom flask was prepared with a magnetic stirring bar, a rubber septum cover, and a nitrogen inlet. 6-hydroxycoumarin (1) (114 mg, 0.7 mmol) and 4 mL of anhydrous DMF were added to the round bottom flask. The solution was stirred and cooled to 0° C. in a salt-ice bath. Sodium hydride (28 mg of 60% mineral oil suspension, 0.7 mmol) was added to the flask and the solution was kept stirring at 0° C. for 30 minutes. Farnesyl bromide (450 µL, 1.66 mmol) in 1 mL of anhydrous DMF was cooled to 0° C. and added drop-wise to the flask through the rubber septum using a syringe. The reaction mixture was left stirring under nitrogen at room temperature for 14 hours. The desired product was isolated via column chromatography using a solvent system of 100% Hexanes, 20:1 Hexanes:Ethyl acetate, 15:1 Hexanes:Ethyl acetate, 10:1 Hexanes:Ethyl acetate, 7:3 Hexanes:Ethyl acetate, and 2:1 Hexanes:Ethyl acetate. The purified product was characterized by NMR spectroscopy ($^1$H-NMR, $^{13}$C-NMR) and high-resolution mass spectrometry (HRMS). $^1$H-NMR (300 MHz, CDCl$_3$): ∂ 1.60-1.76 (12H), 1.96-2.12 (8H), 4.56 (d, 2H, J=6 Hz), 5.09 (m, 2H), 5.48 (t, 1H), 6.43 (d, 1H, J=9 Hz), 692-7.66 (4H); $^{13}$C-NMR (75 MHz, CDCl$_3$): ∂ 15.93, 16.29, 17.70, 25.71, 26.29, 27.04, 39.53, 39.69, 109.75, 117.00, 117.83, 119.14, 123.31, 123.77, 128.33, 131.38, 135.56, 141.96, 143.27, 148.40, 155.33, 161.05. HRMS (CI) Calcd. for C$_{24}$H$_{31}$O$_3$: 367.22733. found: 367.22801.

Example 4

Synthesis of 6-(((2E,6E,10E)-3,7,11,15-tetramethylhexadeca-2,6,10,14-tetraen-1-yl)oxy)-2H-chromen-2-one (5)

Geranylgeraniol (600 mg, 2.07 mmol) and 15 mL of anhydrous tetrahydrofuran were added to a rubber septum covered, oven-dried 50 mL round-bottom flask with a magnetic stirring bar and a nitrogen inlet. The solution was stirred and cooled to −45° C. Upon cooling of this solution, methanesulfonyl chloride (207.5 µL, 2.67 mmol) was added slowly via syringe to the reaction flask. Over a 5-minute period, 574.74 µL of triethylamine was then added via syringe. The resulting suspension was stirred for 45 minutes at −45° C. A solution of lithium bromide (717.5 mg, 8.26 mmol) in 5 mL of tetrahydrofuran was added dropwise via syringe. The suspension was warmed to 0° C. and stirred for 1 hour. The reaction mixture was poured into 8 mL of iced water and the aqueous layer was extracted with ice-cold diethyl ether (3×4 mL). The combined organic extracts were washed with ice-cold saturated NaHCO$_3$ (10 mL) and brine (10 mL), and dried over anhydrous MgSO$_4$. The organic layer was filtered and concentrated in vacuo to obtain the crude geranylgeranyl bromide, which was then used immediately for the following step without further purifications.

An oven-dried 50 mL round bottom flask was prepared with a magnetic stirring bar, a rubber septum cover, and a nitrogen inlet. 6-hydroxycoumarin (1) (474 mg, 2.92 mmol) and 4 mL of anhydrous DMF were added to the round bottom flask. The solution was stirred and cooled to 0° C. in a salt-ice bath. Sodium hydride (117 mg of 60% mineral oil suspension, 2.93 mmol) was added and the solution was stirred at 0° C. for 30 minutes. The crude geranylgeranyl bromide (302.85 mg) from the previous step was dissolved in anhydrous DMF, cooled to 0° C. and added drop-wise to the flask through the rubber septum using a syringe. The reaction mixture was left stirring under nitrogen at room temperature for 14 hours. The desired compound was isolated via preparative thin layer chromatography using a 7:3 Hexanes:Ethyl acetate solvent system. The purified product was characterized by $^1$H-NMR spectroscopy. $^1$H-NMR (300 MHz, CD$_3$COCD$_3$): ∂ 1.54-1.75 (15H), 1.93 (m, 12H), 4.65 (2H), 5.09 (3H), 5.53 (1H), 6.40 (1H), 7.11 (3H), 7.81 (1H).

Example 5

In Vitro Preferential Cytotoxicity and Morphological Change Observation

PANC-1 cells, ranging from passage numbers 30-36 and 40-45, were seeded in 96-well plates at a density of 2.5×10$^4$ cells per well and incubated in fresh Dulbecco's modified Eagle's medium (DMEM, Sigma Aldrich) at 37° C. and 5% CO$_2$ for 24 hours. Cells were then washed with PBS (Sigma Aldrich) and then subjected to the addition of either DMEM or nutrient deprived media absence of glucose, amino acid and serum). Serially diluted coumarin compounds were added to the cells followed by a 24-hour incubation at 37° C. and 5% CO$_2$. Cell morphology was then observed under an inverted microscope. Cells were then washed with PBS, and fresh DMEM and 10% WST-8 cell counting kit solution (Dojindo Molecular Technologies) were added to each well. The cells were incubated for 3-hours at 37° C. and 5% CO$_2$. Absorbance values were measured using a plate reader at 450 nm, and cell viability was calculated using the following equation % Cell viability=[{Abs$_{test\ sample}$−Abs$_{blank}$}/{Abs$_{control}$−Abs$_{blank}$}]*100. The cell viability of compounds 2, 3 and 4 is seen in FIG. 1.

I claim:

1. A method for inhibiting proliferation or survival of a hyperproliferative cell, wherein the hyperproliferative cell is a pancreatic cancer cell, comprising contacting the cell with a coumarin derivative, wherein the coumarin derivative is substituted with at least one substituent at the 6-position, wherein the coumarin derivative is selected from:

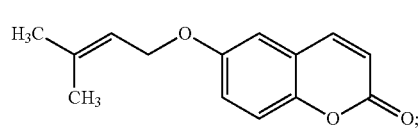
(Compound 2)

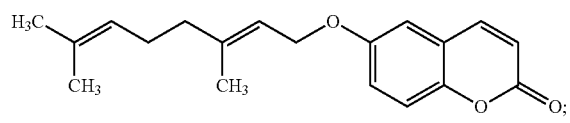
(Compound 3)

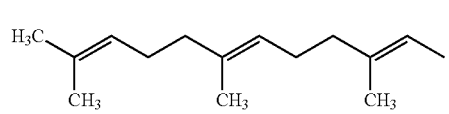
(Compound 4)

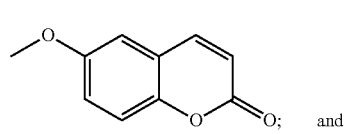
(Compound 5)

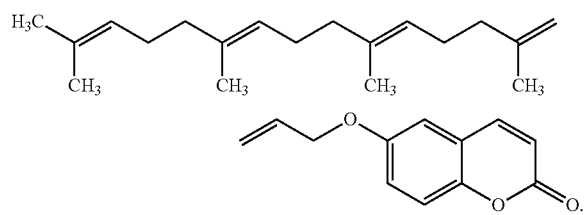

2. A method for inhibiting survival of a pancreatic cancer cell under nutrient starvation conditions, comprising contacting the cell with a coumarin derivative, wherein the coumarin derivative is substituted with at least one substituent at the 6-position, wherein the coumarin derivative is selected from:

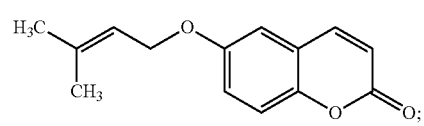
(Compound 2)

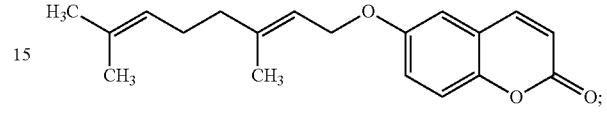
(Compound 3)

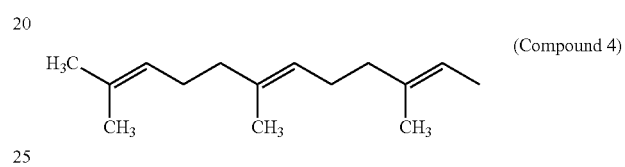
(Compound 4)

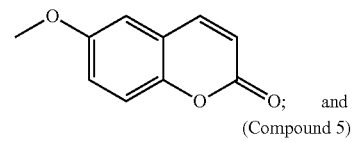
(Compound 5)

3. The method of claim 2, wherein the method is an in vitro method and the cell is a cell in culture.

4. The method of claim 2, wherein the substituent at the 6-position comprises ten or more carbon atoms.

5. The method of claim 4, wherein the substituent at the 6-position comprises fifteen or more carbon atoms.

6. The method of claim 1 or 2 wherein the coumarin derivative is selected from:

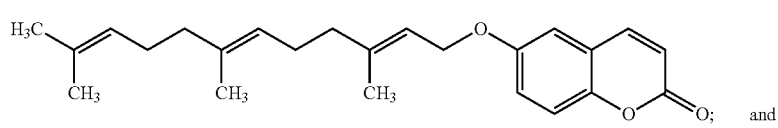
(Compound 4)

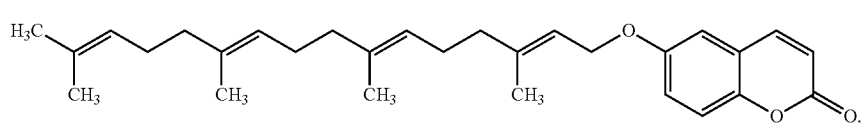
(Compound 5)

7. A composition comprising a coumarin derivative substituted at the 6-position, wherein the coumarin derivative is selected from:

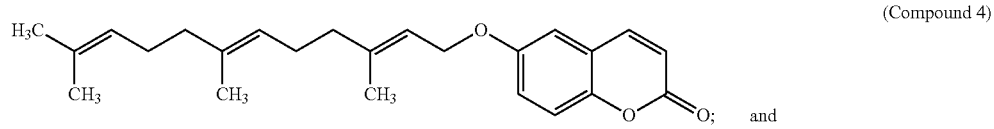
(Compound 4)

and

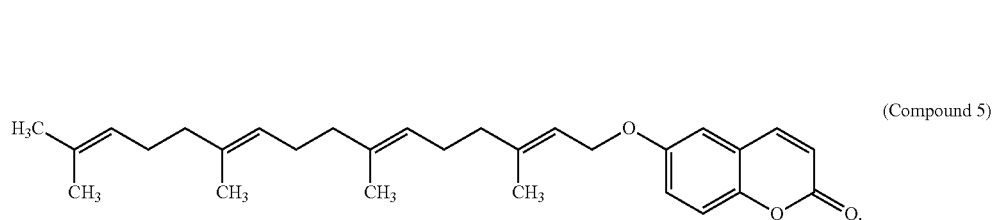
(Compound 5)

8. A pharmaceutical composition comprising a pharmaceutically acceptable excipient and a coumarin derivative selected from:

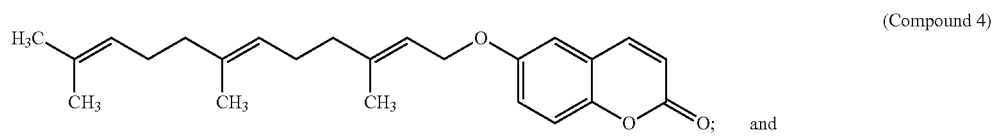
(Compound 4)

and

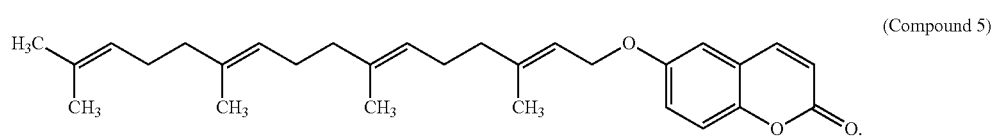
(Compound 5)

9. The composition of claim 7, wherein the coumarin derivative is:

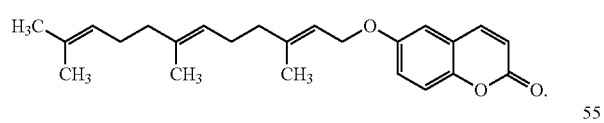
(Compound 4)

10. The composition of claim 7, wherein the coumarin derivative is:

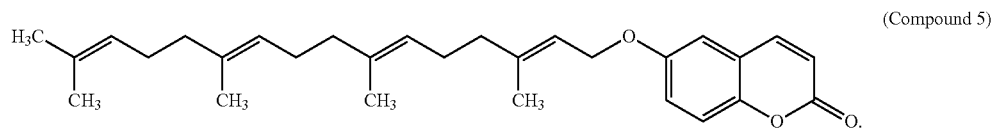 [SMILES: CC(C)=CCC/C(C)=C/CC/C(C)=C/CC/C(C)=C/COc1ccc2oc(=O)ccc2c1]
(Compound 5)

11. The pharmaceutical composition of claim 8, wherein the coumarin derivative is:
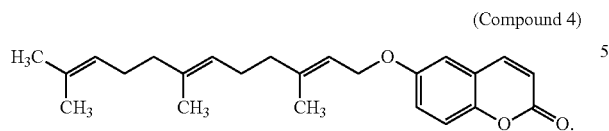
(Compound 4)
12. The pharmaceutical composition of claim 8, wherein the coumarin derivative is:
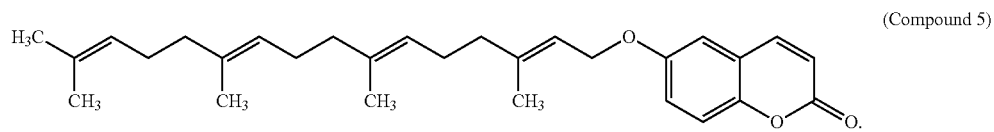 [SMILES: CC(C)=CCC/C(C)=C/CC/C(C)=C/CC/C(C)=C/COc1ccc2oc(=O)ccc2c1]
(Compound 5)
* * * * *